United States Patent
Mather et al.

(10) Patent No.: US 10,336,911 B2
(45) Date of Patent: Jul. 2, 2019

(54) AMPHIPHILIC GRAFT COPOLYMER FOR WATERBORNE SHAPE MEMORY COATINGS

(71) Applicants: Patrick T. Mather, Oxford, PA (US); Xinzhu Gu, Syracuse, NY (US)

(72) Inventors: Patrick T. Mather, Oxford, PA (US); Xinzhu Gu, Syracuse, NY (US)

(73) Assignee: Syracuse University, Syracuse, NY (US)

( * ) Notice: Subject to any disclaimer, the term of this patent is extended or adjusted under 35 U.S.C. 154(b) by 219 days.

(21) Appl. No.: 14/776,098

(22) PCT Filed: Mar. 14, 2014

(86) PCT No.: PCT/US2014/027358
§ 371 (c)(1),
(2) Date: Sep. 14, 2015

(87) PCT Pub. No.: WO2014/152455
PCT Pub. Date: Sep. 25, 2014

(65) Prior Publication Data
US 2016/0032140 A1 Feb. 4, 2016

Related U.S. Application Data

(60) Provisional application No. 61/781,118, filed on Mar. 14, 2013.

(51) Int. Cl.
*C09D 167/04* (2006.01)
*C09D 105/08* (2006.01)
(Continued)

(52) U.S. Cl.
CPC .............. *C09D 167/04* (2013.01); *A61K 8/91* (2013.01); *A61Q 5/04* (2013.01); *A61Q 5/06* (2013.01); *C08B 37/003* (2013.01); *C08G 81/027* (2013.01); *C09D 105/08* (2013.01); *C09D 201/02* (2013.01); *D06M 13/11* (2013.01); *D06M 15/03* (2013.01); *D06M 15/507* (2013.01); *A61K 2800/54* (2013.01); *A61K 2800/95* (2013.01)

(58) Field of Classification Search
None
See application file for complete search history.

(56) References Cited

U.S. PATENT DOCUMENTS 6,160,084 A   12/2000   Langer et al.

OTHER PUBLICATIONS

Chen et al (Chitosan-poly(ε-caprolactone)-poly(ethylene glycol) graft copolymers: Synthesis, self-assembly, and drug release behavior, 2011, J. Biomed. Mater. Res., 96A: 116-124. doi:10.1002/jbm.a.32965).*

(Continued)

*Primary Examiner* — Rachel Kahn
(74) *Attorney, Agent, or Firm* — Bond Schoeneck And King PLLC; David Nocilly; George McGuire

(57) ABSTRACT

A waterborne shape memory polymer coating that gives textiles and fibers good shape memory performance. An amphiphilic, crosslinkable grafted polysaccharide polymer was synthesized and provided in a water dispersion that can be applied to a flexible fibrous material and then crosslinked to yield good shape memory properties. The polymer coating showed good binding to human hair, which could be styled into a permanent shape (e.g., straight) during the crosslinked step. Next, this permanent shape can be styled to a temporary shape (e.g. curly) by heating and styling, and cooling. Finally, the permanent style can be regained by activation with water, heat, or both.

9 Claims, 4 Drawing Sheets

(51) Int. Cl.
   *C09D 201/02*   (2006.01)
   *C08B 37/08*   (2006.01)
   *A61Q 5/06*   (2006.01)
   *C08G 81/02*   (2006.01)
   *D06M 13/11*   (2006.01)
   *D06M 15/03*   (2006.01)
   *D06M 15/507*   (2006.01)
   *A61Q 5/04*   (2006.01)
   *A61K 8/91*   (2006.01)

(56) References Cited

OTHER PUBLICATIONS

Cai et al (Synthesis, characterization and self-assemble behavior of chitosan-O-poly(e-caprolactone), European Polymer Journal 45 (2009) 1674-1680).*

Yu, Haijun, et al., Synthesis and characterization of the biodegradable polycaprolactone-graft-chitosan amphiliphilic copolymers, Biopolymers, Jun. 7, 2006, vol. 83, pp. 223-242, see abstract: See p. 241, right column, lines 1-7, schemes 2-3.

Liu, Li, et al., 'Preparation of chitosan-g-polycaprolactone copolymers through ring-opening polymerization of e-caprolactone onto phythaloyl-protected chitosan', Biopolymers, Apr. 28, 2005, vol. 78, pp. 163-170, see abstract; p. 163, left column; scheme 1.

Liu, Li eg al., 'Synthesis and characterization of chitosan-granft-polycaprolactone copolymers', European polymer Journal, Sep. 9, 2004, vol. 40, pp. 2739-3744, see abstract; p. 2740; scheme 2.

Gu, Xinzhu, et al., 'Entanglement-based shape memory p[olyurethanes: sysnthesis and characterization', Polymer, Oct. 8, 2012, vol. 53, pp. 5924-5934, see abstract.

International Search Report Form PCT/ISA/220, International Application No. PCT/US2014/027358, pp. 1-10, dated Aug. 26, 2014.

* cited by examiner

AMPHIPHILIC GRAFT COPOLYMER FOR WATERBORNE SHAPE MEMORY COATINGS

CROSS-REFERENCE TO RELATED APPLICATIONS

The present application claims priority to U.S. Provisional No. 61/781,118, filed on Mar. 14, 2014.

BACKGROUND OF THE INVENTION

1. Field of the Invention

The present invention relates to fiber coating and, more particularly, to a shape memory polymer coating for hair and other fibers.

2. Description of the Related Art

Polymeric coatings have been used in a wide range of application fields such as automobiles, beauty products, and medical devices. Among the existing hair styling products (gels, sprays, etc) and fabric coatings (e.g., starch), a big disadvantage is that they do not enable reversible styling, or "re-styling", with two styles in memory. Thus, a need exits for the styling products with good shape memory properties and good hair or fabric binding ability.

Shape memory materials are those materials that have the ability to "memorize" a macroscopic (permanent) shape, be manipulated and "fixed" to a temporary and dormant shape under specific conditions of temperature and stress, and then later recover to the original, stress-free, condition under thermal, electrical, or environmental command. This recovery is associated with elastic deformation stored during prior manipulation. Shape memory materials have aroused great attention by scientists and engineers due to their capacity to remember two shapes at different conditions. This gives materials great potential for sensors, actuators, smart devices of great potential for applications that range from consumer products to sporting goods and medical devices. The most prominent and widely used shape memory materials currently are shape memory alloys (SMAs). Their shape memory effect comes from the existence of two stable crystal structures: the high temperature-favored austenitic phase and low temperature-favored (and "yield-able") martensitic phase. Downsides that limit their application exist, including limited recoverable strains less than 8%, inherently high stiffness, high cost, comparatively inflexible transition temperature, and demanding processing and training conditions. Such limitations have provided motivation for the development of alternative materials, especially shape memory properties, the good binding abilities, and the intrinsic nature (non-tacky, odorless, etc) make these materials good candidates for applications as coatings on flexible substrates, such as hair, fabric, paper, sails, plastic film, among others.

BRIEF DESCRIPTION OF THE SEVERAL VIEWS OF THE DRAWING(S)

The present invention will be more fully understood and appreciated by reading the following Detailed Description in conjunction with the accompanying drawings, in which.

Figure 4:
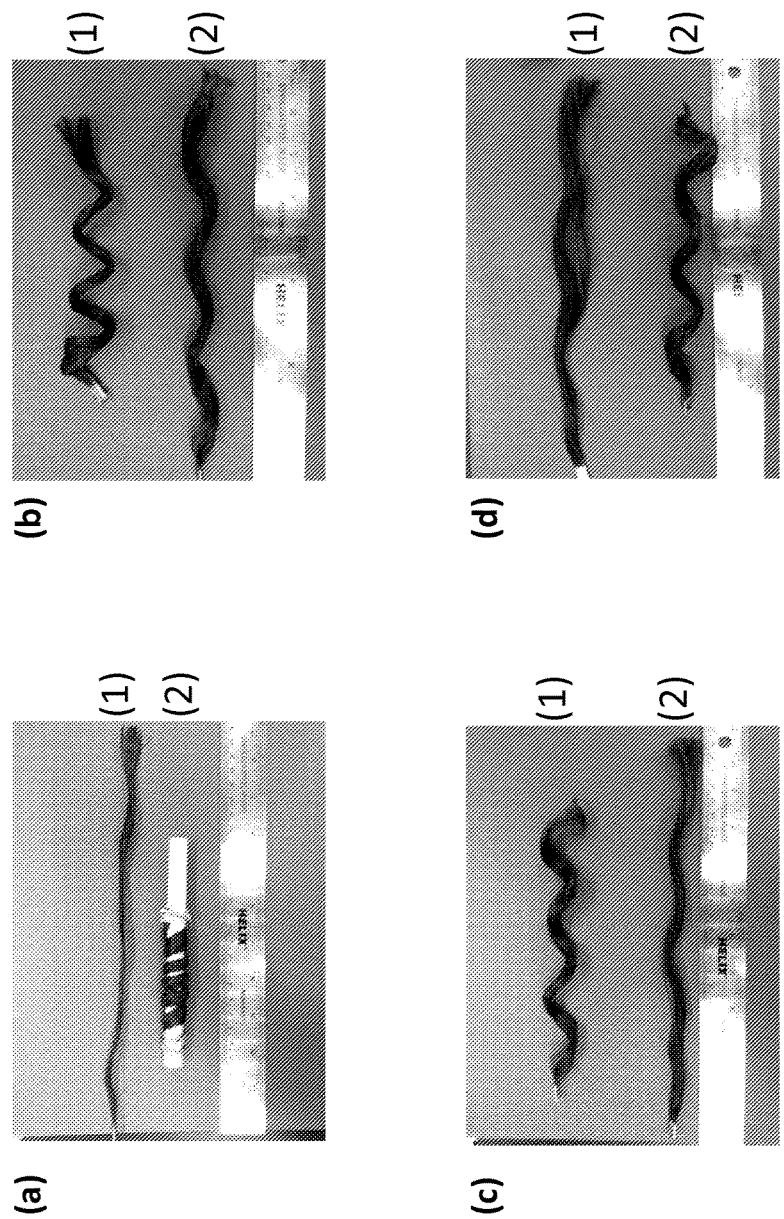

FIG. 4 is a series of photographs illustrating the shape memory behaviors of CS-g-PCL coated hair tresses, crosslinked with BDGE for: (a) permanent shapes ($L_p$); (b) deformed shapes after being deformed at 60° C. and cooled and fixed for 10 min at −20° C. ($L_d$); (c) temporary shapes after hanging at room temperature ($L_d$); (d) recovered shapes after heated at 60° C. ($L_r$), where Sample (1) is the coating having a permanent shape as straight and sample (2) is the coating having a permanent shape as curly.

DETAILED DESCRIPTION OF THE INVENTION

Referring now to the drawings, wherein like reference numerals refer to like parts throughout, the present invention comprises the synthesis of a graft copolymer and the preparation of aqueous dispersion and shape memory testing on hair tresses to provide soft SMPs that are waterborne and gain their softness from a combination of composition and architecture. More specifically, the present invention comprises a graft copolymer approach in which the polymer backbone is a positively charged, water-soluble polysaccharide (chitosan) and the grafting chains are oligomeric, hydrophobic chains capable of crystallizing for a temporary shape.

Figure 1:
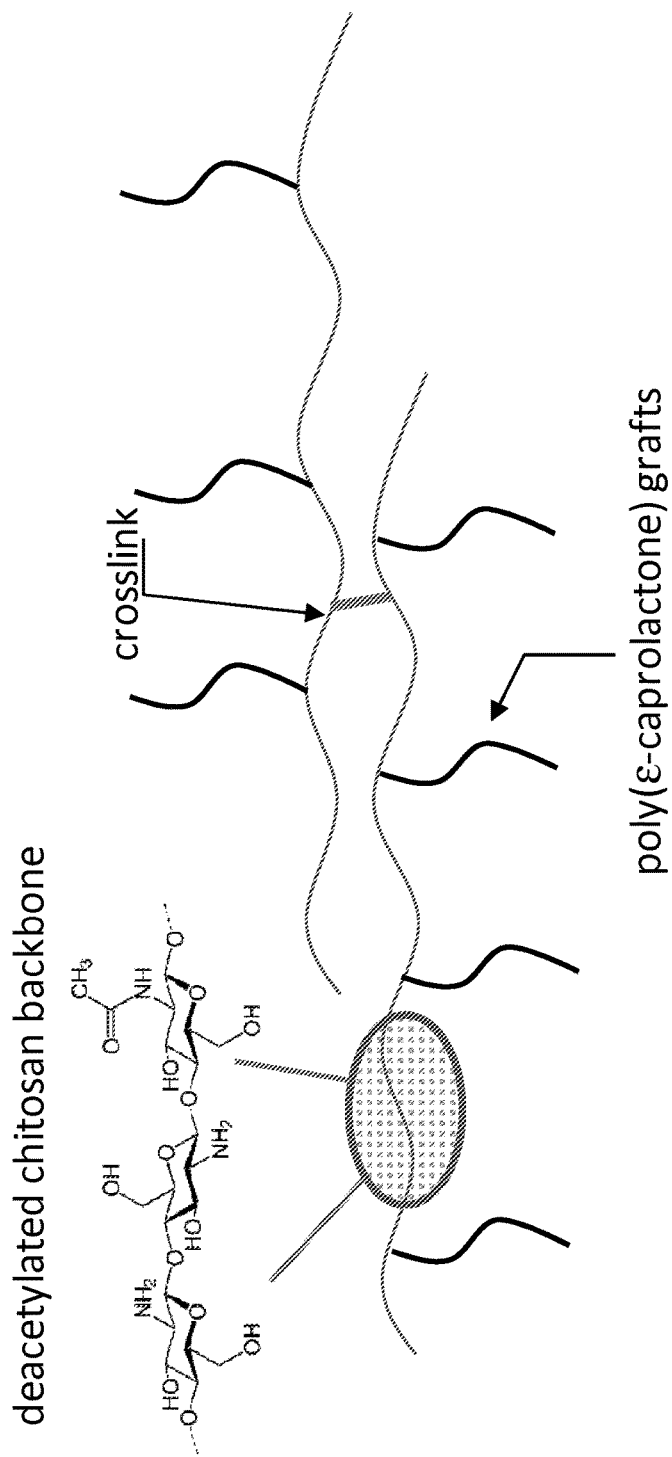
FIG. 1 is a schematic showing the macromolecular design for waterborne SMP.

Referring to FIG. 1, the permanent shape for such a graft copolymer is established by chemical crosslinking during styling. The poly(ε-caprolactone) (PCL) grafts serve for temporary shape setting. Covalent crosslinking is responsible for setting the permanent shape polymeric shape memory materials. Polymeric materials offer intrinsic potential for a shape memory effect, although the mechanisms responsible differ dramatically from those of metal alloys. In SMAs, pseudoplastic fixing is possible through the martensitic de-twinning mechanism, while recovery is triggered by the martensite-austenite phase transition.

In contrast, shape memory polymers (SMPs) achieve temporary strain fixing and recovery through a variety of physical means, while the underlying extensibility is derived from the intrinsic elasticity of polymeric networks. Most shape memory polymers are stiff at temperatures below activation. This is due to the fact that crystallization or vitrification (glass formation) of the entire polymeric materials has been utilized as the means to allow strain fixing. As a consequence, SMPs have not been amenable to applications commonly served by elastomers, such as seals, conformal textiles, among others.

BRIEF SUMMARY OF THE INVENTION

The present invention comprises systems and method to synthesize and test new polymer designs suitable for applications such as waterborne coating products for hair or fabric, or any flexible substrate (hereafter "substrates") engendering shape memory attributes to those substrates.

More particularly, the present invention encompasses a family of new polymer designs centered around use of a natural polymer has been conceived in modular fashion and with a "graft copolymer" architecture. In particular, a graft copolymer is prepared following an approach in which the polymer backbone is a positively charged, water-soluble polysaccharide (deacetylized chitosan) and the grafting chains are oligomeric, hydrophobic chains (in a preferred embodiment, poly(ε-caprolactone)) capable of crystallizing for a temporary shape. The permanent shape for such a graft copolymer is established by chemical crosslinking during styling or otherwise forming. The chitosan backbone, once quaternized, is positively charged and allows water dispersion via micellization along with binding to negative charges on hair or other natural fibers. Shape memory properties of the polymer coatings were tested on hair tresses and demonstrated to be quite promising.

With these characteristics of the present invention, a consumer can apply the polymer from aqueous dispersion and then style the permanent shape (e.g., straightening) at a relatively low temperature (60° C.). Next, the permanent shape can be altered to curly by styling at that temperature. Finally, the permanent style can be regained by heat activation. The good and the PCL grafts are capable of crystallizing for a temporary shape. The chitosan backbone, once quaternized, will be positively charged and allow water dispersion via micellization along with binding to negative charges on hair. Both chitosan and the PCL—polymers encompassed by the present invention—are known to be non-toxic and have been widely studied for their applications in pharmaceutical, cosmetics, biomedical, agricultural, and food industries.

Figure 2:
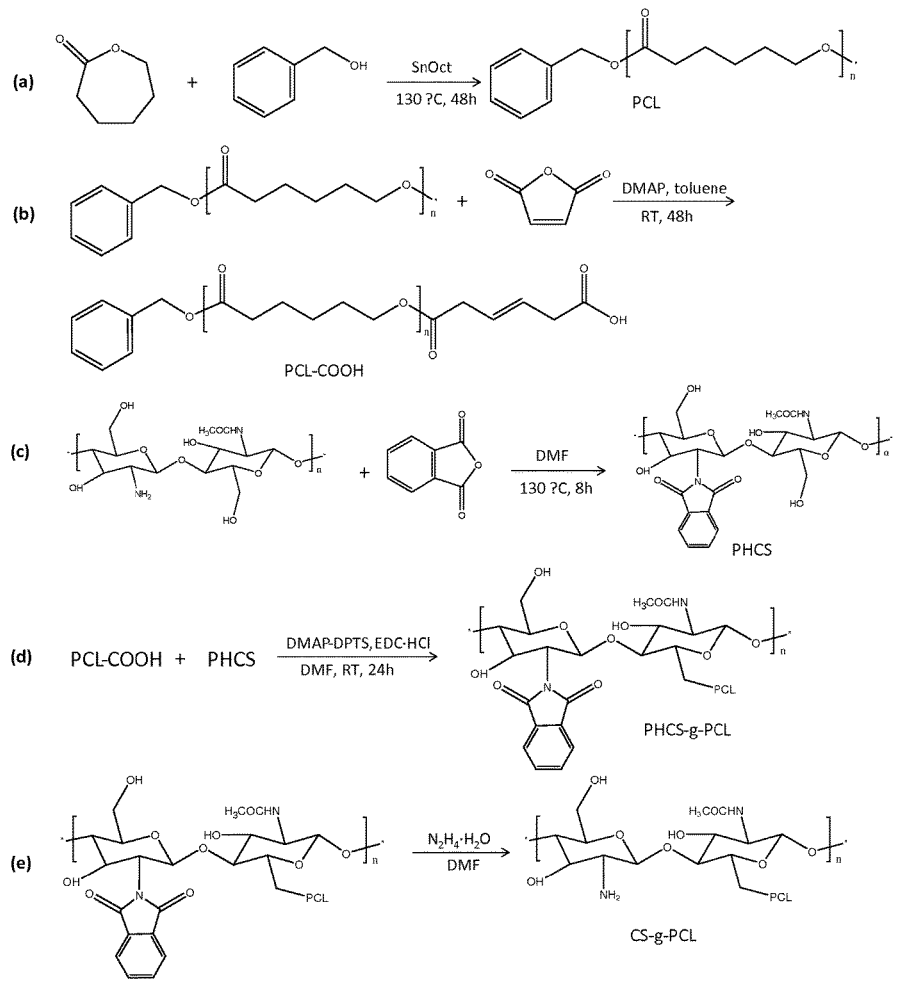
FIG. 2 is a series of chemical diagrams showing the synthesis of: (a) PCL initiated by benzyl alcohol; (b) Monocarboxy-capped PCL (PCL-COOH); (c) phthloychitosan (PHCS); (d) graft copolymers (PHCS-g-PCL); and (e) CS-g-PCL by deprotecting PHCS-g-PCL.
Figure 3:
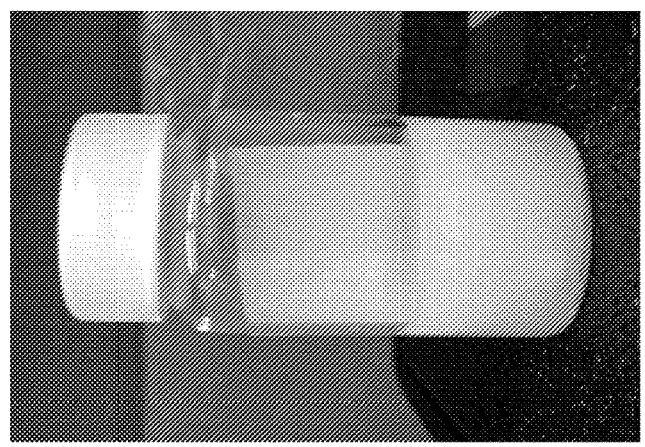
FIG. 3 is a series of photographs showing: (a) CS-g-PCL obtained as a yellow powdery material from the synthesis steps shown in FIG. 2; and (b) Aqueous dispersion (2%, w/v) of the CS-g-PCL in 1% acetic acid aqueous solution (pH 2.8) under stirring for 24 hours.
Figure 3:
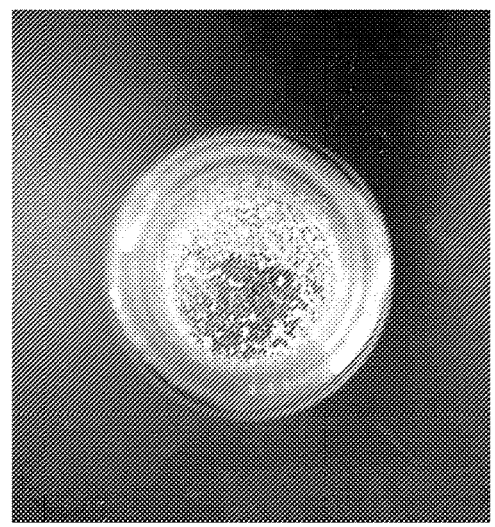

The graft copolymers of chitosan with PCL are prepared via a protection-graft-deprotection route, by the esterification of phthaloyl-protected chitosan (PHCS) with PCL-COOH. Following that phthaloyl groups are deprotected to give the free amino groups. In this way, good control over the molecular weight of the grafting chains (PCL) is possible. The synthetic strategy to make the graft copolymer (CS-g-PCL) may be seen in FIG. 2, which shows the synthesis of: (a) PCL initiated by benzyl alcohol; (b) Monocarboxy-capped PCL (PCL-COOH); (c) phthloychitosan (PHCS); (d) graft copolymers (PHCS-g-PCL); and (e) CS-g-PCL by deprotecting PHCS-g-PCL. The final products (CS-g-PCL) are yellow powdery materials, as seen in FIG. 3(a). The thermal behavior of the graft copolymer was characterized by differential scanning calorimetry (DSC). A melting transition was observed around 50° C., indicating successful grafting of PCL chains onto the chitosan backbone.

The graft copolymer (CS-g-PCL5k) was then dispersed in 1% acetic acid (a good solvent for deacetylized chitosan, but poor solvent for PCL grafts) under stirring for 24 hours to obtain the water dispersion. The size of self-aggregates and their distribution were measured using a Malvern Instrument Zetasizer Nano S laser scattering system. The mean diameters of aggregates range from 200 to 400 nm, with a unimodal size distribution. The resulting dispersion is shown in FIG. 3(b).

Dark brown hair tresses were with average weight of 2 grams were used to test the present invention. Hair tresses were coated with 4 ml aqueous dispersion (polymer: ~40 mg/g of hair) using a pipette and dried in the hood at RT. Dimethyl 3-3, dithio bis' propionimidate (DTBP), together with two diepoxide-based bifunctional linkers, neopentyl glycol diglycidyl ether (NGDE) and 1,4-butanediol diglycidyl ether (BDGE) were used to crosslink the chitosan chains via the reactive amino group on the chitosan backbone. Other diepoxide molecules may serve as suitable crosslinkers. The permanent shapes were set to be either straight or curly at this step. The crosslinker solution was applied onto the hairs and crosslinked at room temperature for 24 hours. The amount of crosslinking solution applied for different crosslinkers were shown in Table 1 below. It was noted that hair tresses coated with copolymer dispersion felt soft and can easily be combed through.

TABLE 1

The amount of crosslinking solution applied for different crosslinkers.

| Crosslinker | Applied Amount |
| --- | --- |
| DTBP | 0.5 wt % DTBP in 6 ml Tris buffer |
| NGDE | 2.5 ml NGDE + 2.5 ml isopropanol |
| BDGE | 0.8 ml BDGE + 1.6 ml $H_2O$ |

Shape memory properties of the polymer coating were investigated on hair tresses. The length of the permanent shape was recorded as $L_p$. Hair tresses were deformed by either hanging a weight (straight as temporary shape) or by wrapping around a plastic rod (curly as temporary shape) at 60° C. Samples were then transferred to a freezer (−20° C.) for 10 min to allow the crystallization of PCL phases. Then the load was removed, and the samples' lengths were measured ($L_d$). Shape fixing ability was evaluated by hanging samples at room temperature for 30 min, and the length of the tresses at the end of this stage were measured ($L_t$). Finally, shape recovery was induced by hanging tresses at 60° C. for 10 min to a recovered length, $L_r$. The fixing ($R_f$) and recovery ($R_r$) ratios were calculated for each sample using Equations 1 and 2:

$$R_f(\%) = \left(\frac{L_t - L_p}{L_d - L_p}\right) \cdot 100 \qquad (1)$$

$$R_r(\%) = \left(\frac{L_r - L_t}{L_p - L_t}\right) \cdot 100 \qquad (2)$$

The tress crosslinked with DTBP showed moderate recovery behavior with $R_r$ of 75% when the permanent shape was programmed to be straight. However, in this case the fixing ratio was low ($R_f$=45%). When setting the permanent shape as curly, the recovery ability ($R_r$) decreased to 15%, while $R_f$ reached 100%. The different fixing and recovery behaviors of these two scenarios were attributed to the effect of gravity. After switching the crosslinker from DTBP to the two diepoxide-based bifunctional linkers (i.e. NGDE and BDGE), the recovery ratios significantly improved to 46% and 97% for permanent straight shape and permanent curly shape, respectively, indicating higher crosslinking density was achieved.

Referring to FIG. 4, the shape memory behaviors of CS-g-PCL coated hair tresses, crosslinked with BDGE, may be seen as follows: (a) permanent shapes ($L_p$); (b) deformed shapes after being deformed at 60° C. and cooled and fixed for 10 min at −20° C. ($L_d$); (c) temporary shapes after hanging at room temperature ($L_t$); (d) recovered shapes after heated at 60° C. ($L_r$), where Sample (1) is permanent shape as straight and sample (2) is permanent shape as curly.

The present invention could be used as a coating on flexible substrates, including hair, human skin, fabric, paper, sails, plastic film, botanical plant leaves, wire, monofilament, thread, yarn, elastomer (rubber), among others.

What is claimed is:

1. A fiber having a graft copolymer coating thereon, the coating comprising a covalently cross-linked graft copolymer produced by reacting, at room temperature:
   a graft copolymer comprising a backbone of deacetylized chitosan having a plurality of reactive amino groups and a side chain comprising oligomeric poly (ε-caprolactone) grafted onto said backbone, and a diepoxide linker selected from the group consisting of neopentyl glycol diglycidyl ether (NGDE) and 1,4-butanediol diglycidyl ether (BDGE).

2. The coated fiber of claim 1, wherein a melting transition temperature of the graft copolymer is about 50° C.

3. A method of providing shape memory to fibers, comprising the steps of:

coating, onto at least one fiber, an aqueous dispersion of a graft copolymer comprising a backbone of deacetylized chitosan having a plurality of reactive amino groups and a side chain comprising oligomeric poly (ε-caprolactone) grafted onto said backbone, and applying, at room temperature, a diepoxide linker selected from the group consisting of neopentyl glycidyl ether (NGDE) and 1,4-butanediol diglycidyl ether (BDGE) to covalently cross-link the reactive amino groups of the chitosan.

4. The method of claim 3, wherein said aqueous dispersion comprises said graft copolymer dispersed in water via micellization.

5. The method of claim 3, wherein a melting transition temperature of the graft copolymer is about 50° C.

6. The method of claim 3, further comprising the step of arranging said at least one fiber into a first predetermined configuration prior to cross-linking said chitosan backbone.

7. The method of claim 6, further comprising the step of arranging said at least one fiber into a second, different predetermined configuration after cross-linking said chitosan backbone.

8. The method of claim 7, further comprising the step of returning said coated fiber to said first predetermined configuration from said second predetermined configuration.

9. The method of claim 8, wherein said step of returning said coated fiber to said first predetermined configuration comprises heating said at least one fiber.

* * * * *